United States Patent [19]

Muoio

[11] Patent Number: 5,740,560
[45] Date of Patent: Apr. 21, 1998

[54] NON-FOULING EYEWEAR FOR HIGH POLLUTION ENVIRONMENTS

[76] Inventor: Frank J. Muoio, 88 Maple St., Darien, Conn. 06820

[21] Appl. No.: 499,767

[22] Filed: Jul. 7, 1995

[51] Int. Cl.⁶ .................................. A61F 9/02; G02C 9/00
[52] U.S. Cl. .......................... 2/434; 2/13; 2/454; 351/47
[58] Field of Search ............................... 2/434, 432, 431, 2/441, 443, 454, 13; 128/858; 351/47, 44, 57

[56] References Cited

U.S. PATENT DOCUMENTS

| | | | |
|---|---|---|---|
| 2,759,394 | 8/1956 | Evans | 2/432 X |
| 4,138,746 | 2/1979 | Bergmann | 2/434 X |
| 4,716,601 | 1/1988 | McNeal | 2/434 |
| 4,797,956 | 1/1989 | Boyce | 128/858 X |

*Primary Examiner*—Peter Nerbun
*Attorney, Agent, or Firm*—Handal & Morofsky

[57] ABSTRACT

Protective goggles which comprise a transparent protective member made of a polarizing lens with a polarizing characteristic oriented to reduce glare are disclosed. A transparent anti-fouling member is configured to overlie at least a portion of the transparent protective member. An adhesive is disposed on the transparent anti-fouling member. The adhesive is adapted to allow the transparent anti-fouling member to be adhered to the transparent protective member.

14 Claims, 8 Drawing Sheets

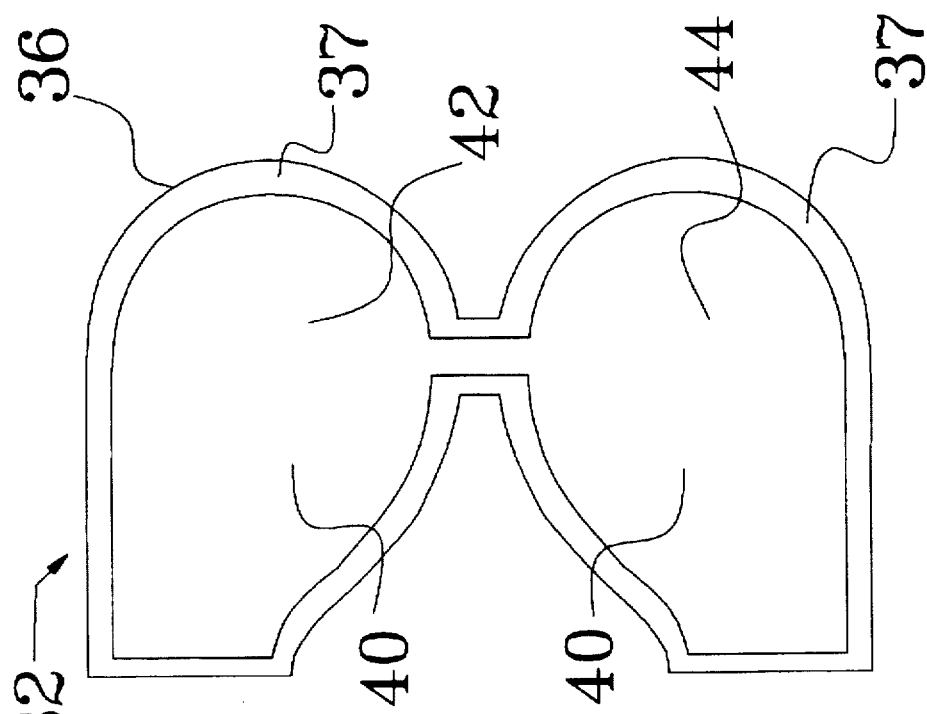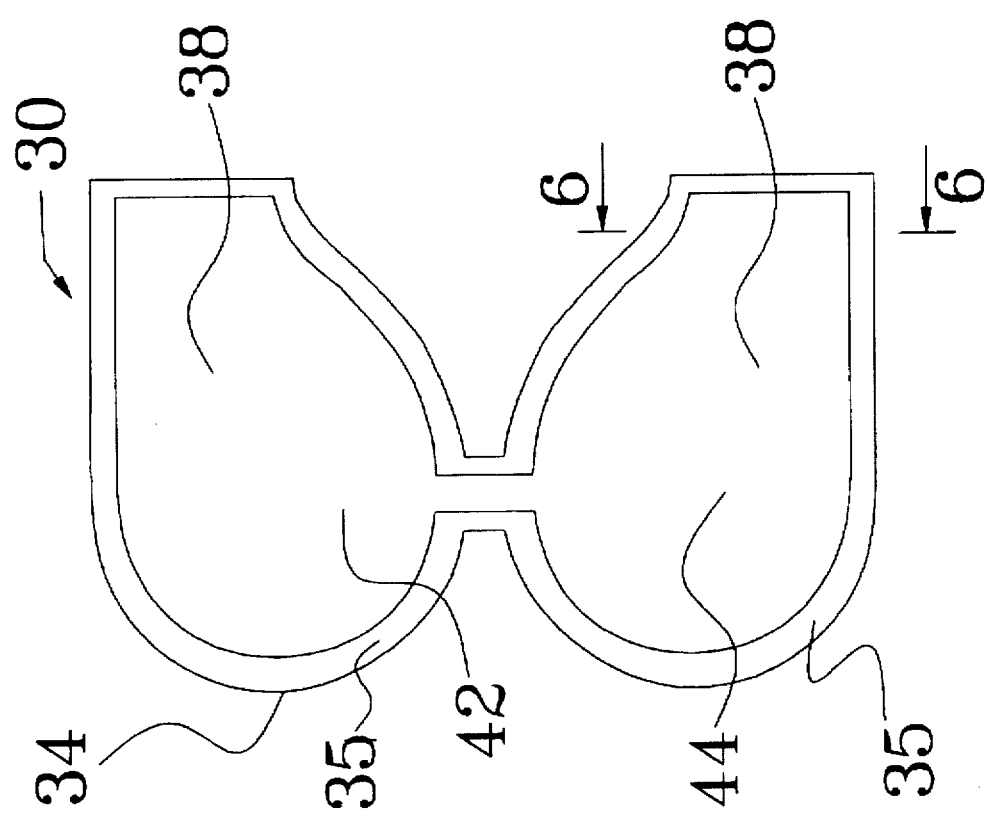

5,740,560

NON-FOULING EYEWEAR FOR HIGH POLLUTION ENVIRONMENTS

TECHNICAL FIELD

The present invention relates to eyewear which protects against flying objects, airborne contaminants, ultraviolet radiation, glare and other hazards, while minimizing the effects of environmental glare and maintaining excellent view-through characteristics in poor visibility environments.

BACKGROUND ART

Eye injury is the cause of lost hours of productivity in the workplace. These lost hours translate into higher production costs which lead to higher costs to consumers with no commensurate benefit. It is therefore desirable to identify activities when such injury is likely, determine the particular hazards presented, and design a solution which addresses those hazards to as great an extent as possible with the best achievable economy.

Eye injuries can occur when performing hazardous tasks. Such tasks include those that result in ejection of mechanical hazards or that cause sometimes noxious particulates to become airborne, for example, cutting or grinding of metals or spraying of coatings, such as paints epoxies, and rust inhibitors. Airborne particulates are also a hazard in working environments where dust is commonplace, such as in wood shops. These airborne particulates may strike the cornea of the eye thereby requiring medical attention and often extended recovery periods. In the case of some materials, mere presence in the eye may cause other problems such as irritation or even tissue damage. Obviously long term repetitive exposure can cause yet additional, and often more serious problems.

An additional troublesome characteristic presented by many airborne materials, such as adhesives, greasy grindings, paint and oil spray, is the tendency of these materials to adhere to the eye.

Because of the sensitivity of the eyes to injury, protective eyewear is in common use. However, even protective eyewear can create an additional problem, that is, the adhesion of materials in the air to the eyewear, impairing visibility, and increasing the likelihood of accidents thereby requiring the eyewear to be cleaned. In the case of non-sticky particulates like dust or clean grindings, a single quick wipe takes care of the problem. However, if grease is involved, soap and water is needed and the added trouble may mean cleaning is not done often enough and the dirty glasses will be used even though vision is impaired, a dangerous condition that will increase the likelihood of an accident occurring.

The problem is yet further complicated by such materials as paint, which can only be removed with a solvent. Unfortunately, often the necessary cleaning solvents will mar the lenses and in such cases the eyewear must be discarded.

Prior art systems have proposed protective eyewear that will protect the eyes, but become damaged and non-usable in a short time due to particulates adhering to or striking non-resistant lenses (see for example U.S. Pat. No. 4,850,058 issued to Chesan Cheng on Jul. 25, 1989). While these systems provide eye protection, the eyewear itself must be changed frequently due to surface scratches.

Other prior art systems have been shown to protect both the eyes and the eyewear through the use a plurality of replaceable films that shield the eyewear (see for example U.S. Pat. No. 4,076,373 issued to Anthony L. Moretti on Feb. 28, 1978), but fail to provide a solution to the problem of visibility inhibited by glare. In fact these systems due to the use of a plurality of replaceable films being stacked over the eyewear cause further visibility problems. The surfaces of the individual layers cause their own reflection, diffraction, and visual distortion. Still other systems provide eye protection and glare reduction but make no provision for the protection of the eyewear itself. However, such prior art systems fail to solve other problems. High density airborne particulates, such as spray paint, irrespective of their adhesive qualities, cause other problems besides injury. Airborne particulates cause light to scatter in a random fashion thereby reducing the ability to see the surface upon which the work is being performed.

Moreover, because this distributes the source of light over a larger area, a great deal of light is reflected back onto the workpiece, resulting in reflection at angles less than the critical angle, resulting in polarized reflections of a relatively high intensity, regardless even of the color of the workpiece. Such is the case, for example, when spray painting the surface of a lightly colored car. Given that it is necessary to be able to make out the finest details of the work, so that the newly painted surface matches the surfaces that have the original manufactured finish, the glare in the lighting of the workpiece can easily result in unacceptability in the quality of the work. The use of brightly lit modern spray booths, far from improving the situation, actually only further exacerbates the problem. Thusly, while the eyewear is effective in reducing bodily injuries, the protective eyewear itself presents its own problems.

SUMMARY OF THE INVENTION

The inventive system hereinafter described achieves a solution to the aforementioned problems by a unique combination of elements while not in itself creating other problems. The system utilizes an apparatus which provides for eye protection particularly effective against adhesive particles while at the same time addressing the adhesion effectively through the use of a transparent shield. This shield not only acts as a physical barrier to airborne particulates but is constructed to reduce glare utilizing the principle of selective absorption. Conversely, the shield can be a clear while the lenses themselves utilize the principle of selective absorption. The problem of adhesive particles sticking to the surface of the lenses has been eliminated thereby eliminating the need to clean and subsequently expose the lenses to the possibility of damage due to the use of solvents. The possibility of damage due to scratching has also been greatly mitigated thereby reducing the likelihood that the eyewear will have to be replaced. These problems have been solved while not creating the further problems that prior inventions have created, namely, visual distortion.

BRIEF DESCRIPTION OF THE DRAWINGS

One way of carrying out the invention is described in detail below with reference to drawings which illustrate only one specific embodiment of the invention and in which:

FIG. 4 is a plan view of a preferred embodiment of the left lens shield;

FIG. 5 is a plan view of a preferred embodiment of the right lens shield;

DETAILED DESCRIPTION OF THE PREFERRED EMBODIMENTS

Figure 1:
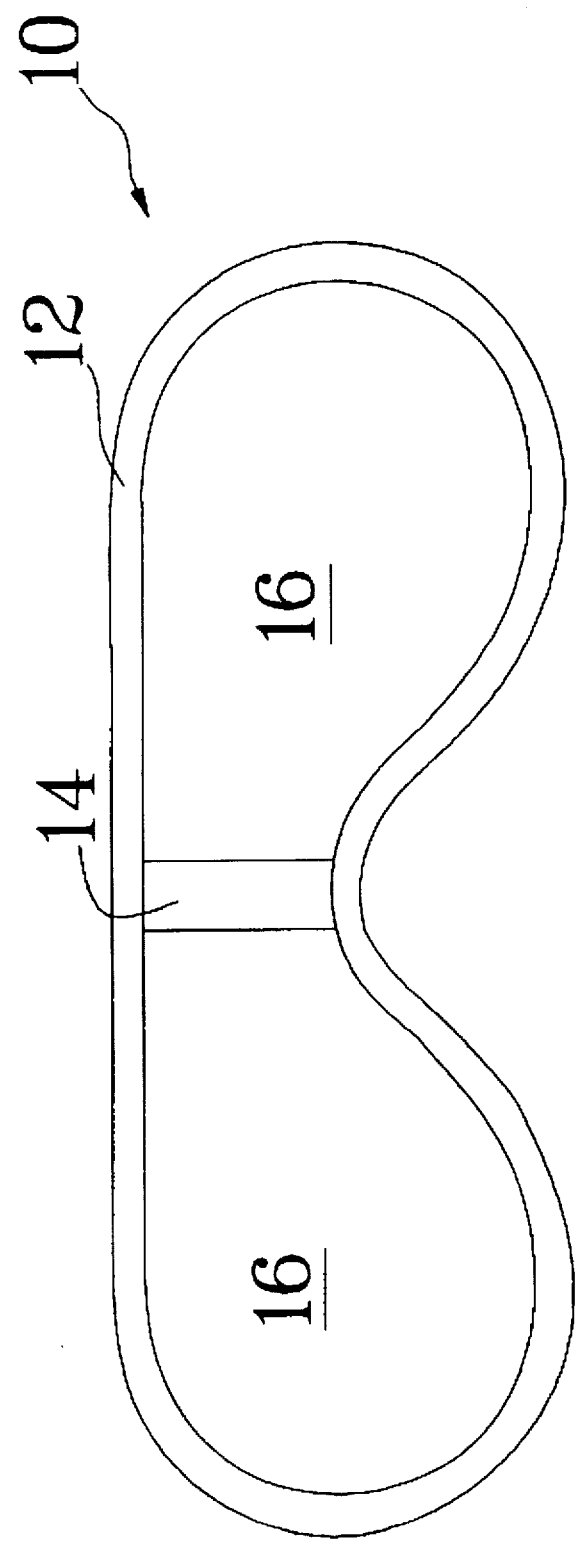
FIG. 1 is a front view illustrating the construction of a preferred embodiment of the inventive system.

Turning to FIG. 1 a pair of glasses incorporating the system of the present invention is illustrated. The inventive glasses 10 comprise a frame 12. Frame 12 includes a cross linking member 14 which gives the structure added strength and rigidity. The glasses 10 also include lenses 16 which are disposed within frame 12.

Figure 2:
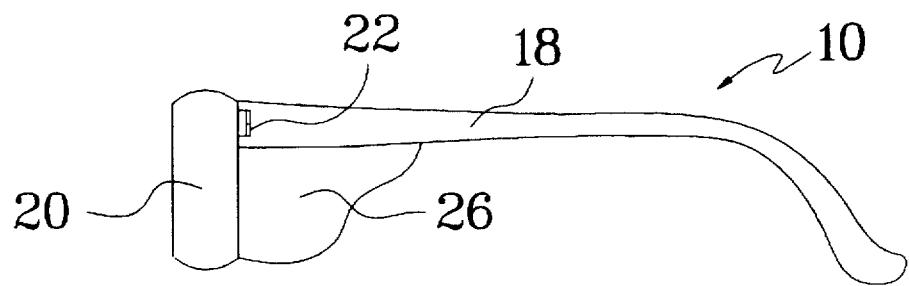
FIG. 2 is a side view illustrating the construction of a preferred embodiment of the inventive system.
Figure 3:
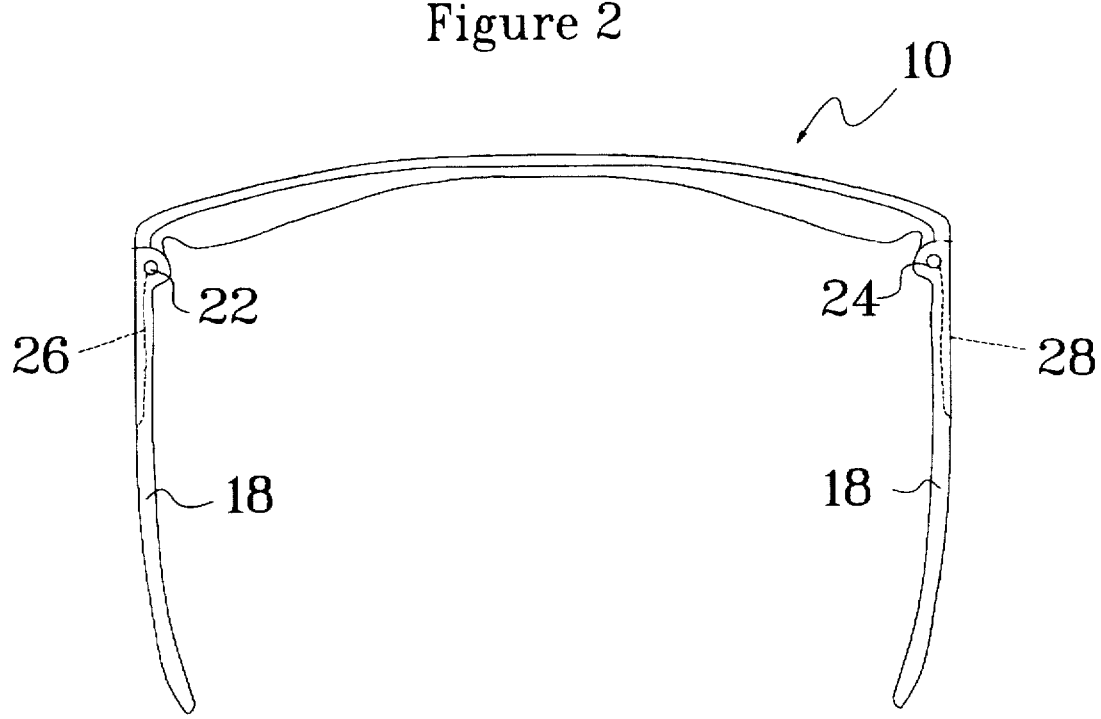
FIG. 3 is a plan view illustrating the construction of a preferred embodiment of the inventive system.

Reference is now made to FIGS. 2 and 3. Frame 12 also includes a pair of arms 18 which are connected to the front 20 of frame 12 by a pair of hinges 22 and 24. Protection from hazards on the side of the user is provided by a pair of side shields 26 and 28. Side shields 26 and 28 are integral with arms 18, as illustrated in FIG. 2 and in FIG. 3.

In accordance with the invention, glare is reduced by the provision in lenses 16 of a polarizing function. In accordance with the invention, lenses 16 are made of a plastic polarizing material which is well known in the art. Such materials are used in the manufacture of cardboard frame 3 D glasses for movies, and in polarizing clip-on lenses for eye glasses and in inexpensive polarizing glasses.

In the alternative, lenses 16 may be made of any clear material sandwiched to a thin polarizing film as is conventionally done in optometric applications.

The structure of the inventive glasses 10 is completed by a pair of replaceable lens covers or shields 30 and 32, as illustrated in FIGS. 4 and 5. Covers 30 and 32 both comprise a transparent substrate 34 and 36, respectively. Substrates 34 and 36 are secured in position by adhesive patches 38 and 40, respectively. Shields 30 and 32 include upper portions 42 and lower portions 44. The upper portion 42 is meant to be adhered to the inside surface of the lenses. Likewise, the lower portion 44 of each of the shields is intended to be adhered to the outside surface of the lenses. Accordingly, the adhesive that forms patches 38 and 40 is disposed over the substrates 34 and 36 of the shields, respectively.

Figure 6:
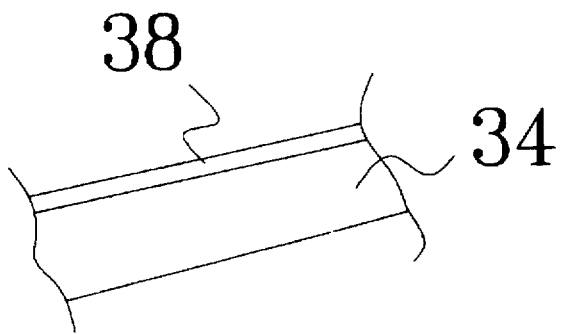
FIG. 6 is a section view of a preferred embodiment of the left lens shield.

The construction of shields 30 and 32 may be more easily understood with reference to FIG. 6. More particularly, the substrates 34 of the shields are made of a flexible plastic material, such as Mylar plastic. The material of which substrate 34 is made must be highly transparent in order to have good optical characteristics. Materials may also include poly vinyl chloride, poly vinyl acetate, or any other similar material. The adhesive 38 must be relatively unaggressive. Appropriate adhesives would be the so called temporary adhesives manufactured by 3M Corp. of Minneapolis, Minn. and incorporated in their removable note pad products sold under the trademark Post-it.

Figure 7:
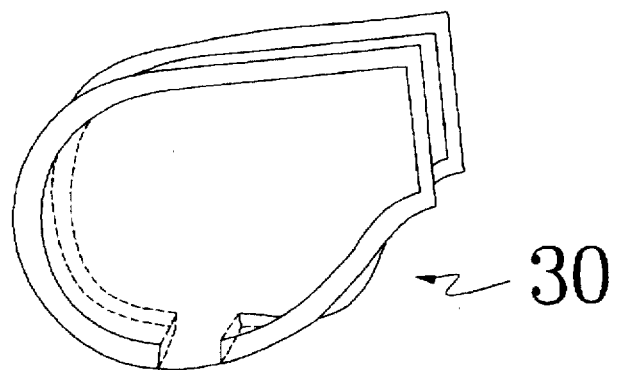
FIG. 7 is a view of a preferred embodiment of the left lens shield as applied to the lens.

As can be seen with reference to FIG. 7, when it is desired to employ the apparatus of the present invention, one takes one of the shields 30 or 32 and folds it in to the configuration illustrated in FIG. 7. In this configuration it may be positioned with the lens 16 of a pair of glasses between it, as is illustrated in the side view of FIG. 8.

Figure 8:
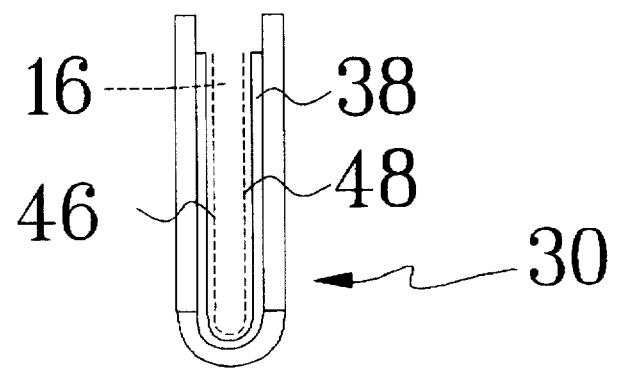
FIG. 8 is a cross section view of a preferred embodiment of the lens shield as applied to the lens.
Figure 9:
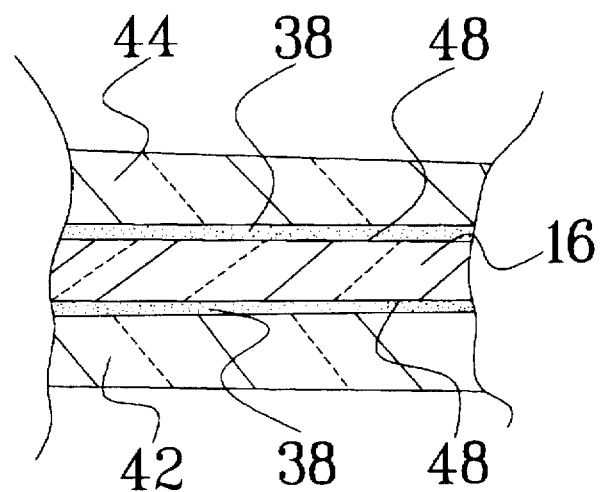
FIG. 9 is a magnified cross section view of a proffered embodiment of the lens shield as applied to the lens.

After the shield 30 is folded, as illustrated in FIGS. 7 and 8, and positioned around a lens 16, it is pressed into intimate contact with the front 46 and the rear 48 of the lens. The result is to form a sandwich, as illustrated in FIG. 9 which is a cross-sectional view. As can be seen with reference to FIG. 9, the sandwich comprises a lens 16 to which the lower portion of shield 44 is adhered by adhesive 38. Likewise upper portion of shield 42 is adhered by adhesive 38.

Figure 10:
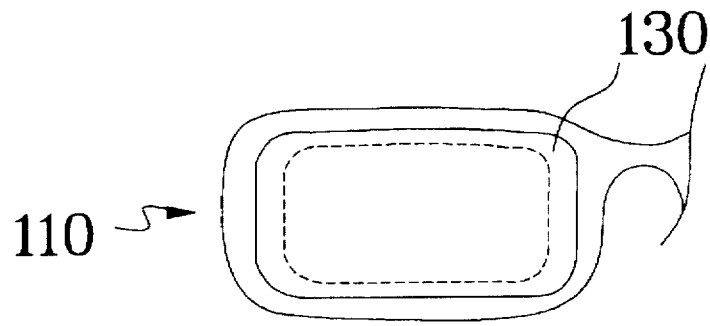
FIG. 10 is a front view of an alternative embodiment as applied to the lens.

By applying shields for 30 and 32 to the lenses in the inventive system, both sides of the lenses are protected from paint and other particulate material. Alternatively, it is sufficient in many applications to apply a protective shield 130 to the outside surface of a pair of glasses 110 as illustrated in FIG. 10.

Figure 11:
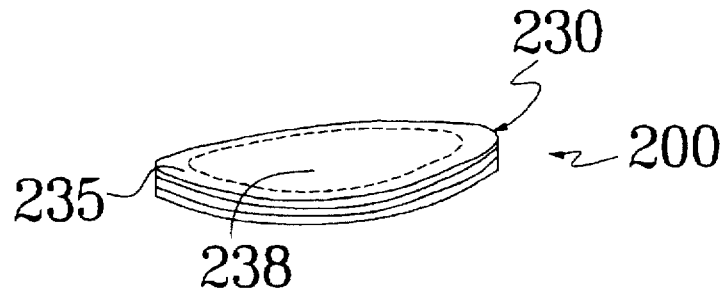
FIG. 11 is a orthogonal view of a pad of lens shields.

Referring to FIG. 11, in accordance with the present invention, it is contemplated that the shields will be made available in the form of a pad which will allow one shield at a time to be removed. While the embodiment illustrated in FIG. 11 corresponds to the single lens shield of FIG. 10, the shields illustrated in FIG. 4, FIG. 5, FIG. 16 and FIG. 17, may also be put in pad form, being die cut in the same manner as a paper pad of customized configuration. The pad 200 is particularly easy to use because the peripheral portions 235 of the individual shields 230 do not have adhesive, and thus may be grasped easily at any point by a user. The adhesive 238 is applied to the center region of shield 230.

Figure 12:
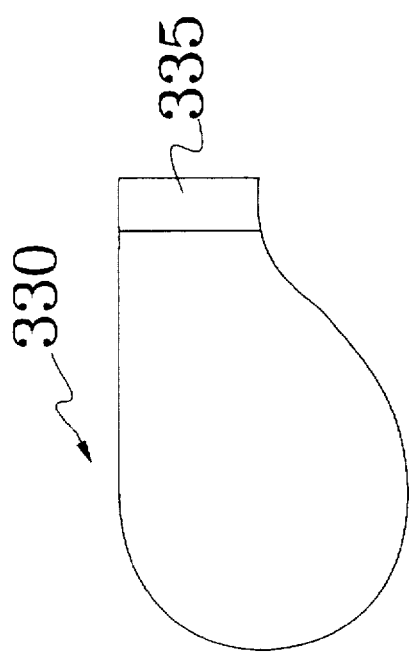
FIG. 12 is a plan view of an alternative lens shield.

In principle it is also possible that the portion 335 of a shield 330 which does not have adhesive on it be limited to a small tab, as is illustrated in FIG. 12.

Figure 13:
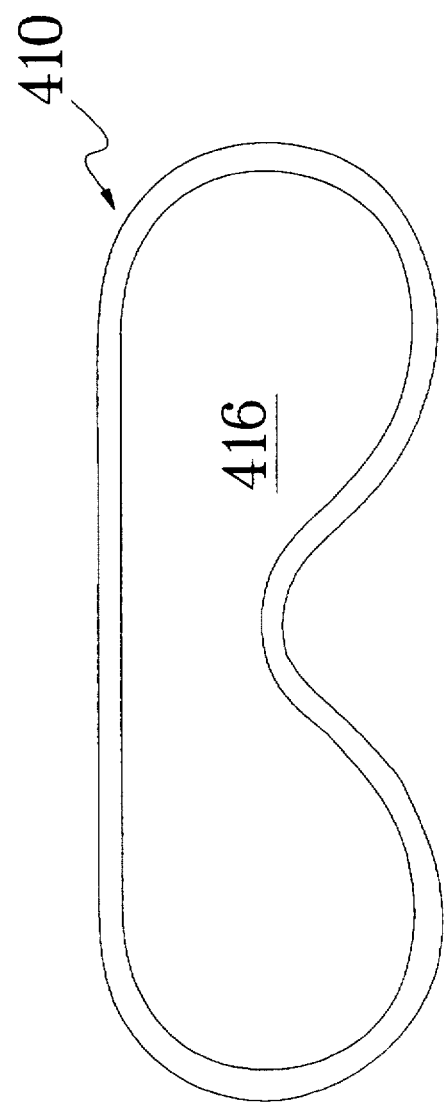
FIG. 13 is a front view of an alternative embodiment of a the inventive device.
Figure 14:
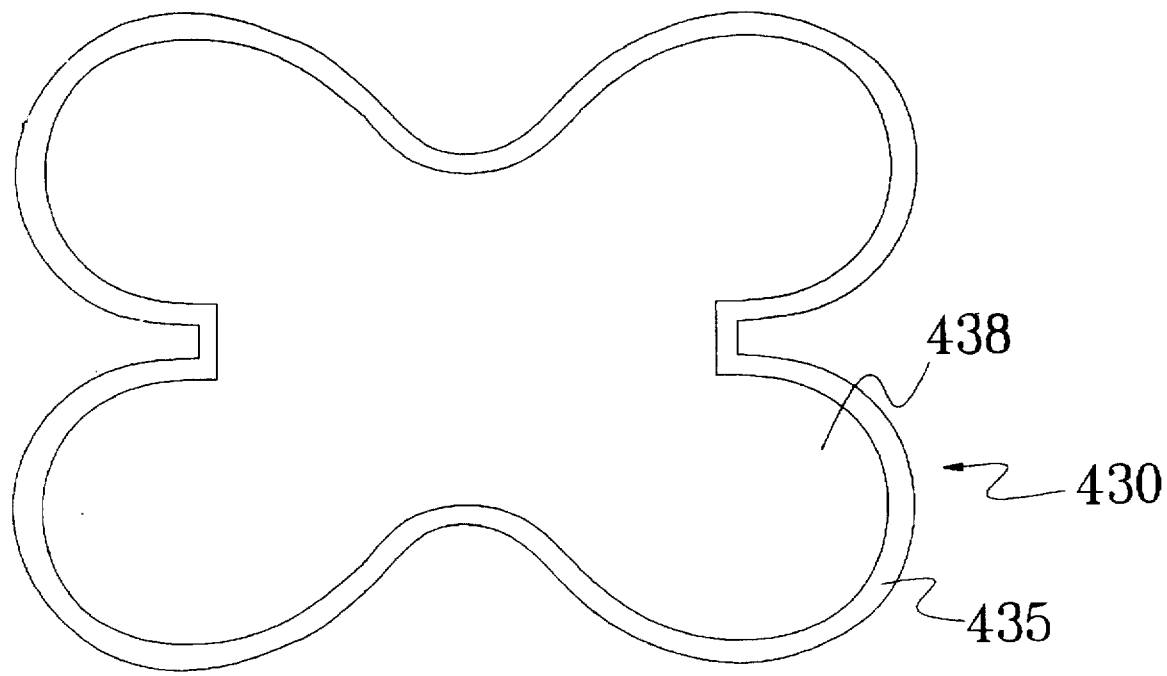
FIG. 14 is a plan view of an alternative shield as designed for the alternative embodiment of the inventive device.

Still yet another possibility is illustrated in FIGS. 13 and 14. In this embodiment, a pair of glasses 410 is provided with a single large lens 416. Accordingly, as is illustrated in FIG. 14, a single shield 430 is employed for both sides of lens 416. Shield 430, in similar fashion to the shields of the other embodiments, has an adhesive area 438 surrounded by a peripheral portions 435 which does not have adhesive attached to it and allows grasping by a user to remove from a pad and also to allow easy removal from a pair of glasses so that the shield may be disposed of and replaced with a new clean clear transparent plastic shield.

Figure 15:
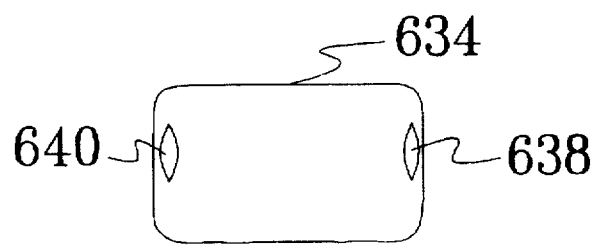
FIG. 15 is a plan view of an alternative embodiment of a lens shield.

Another embodiment of the lens shield is shown in FIG. 15 wherein adhesive 638 and 640 is disposed on two discrete areas of substrate 634.

Again, the shields in FIG. 14 and FIG. 15 can be die cut and made available in the form of a pad similar to that seen in FIG. 10.

Figure 17:
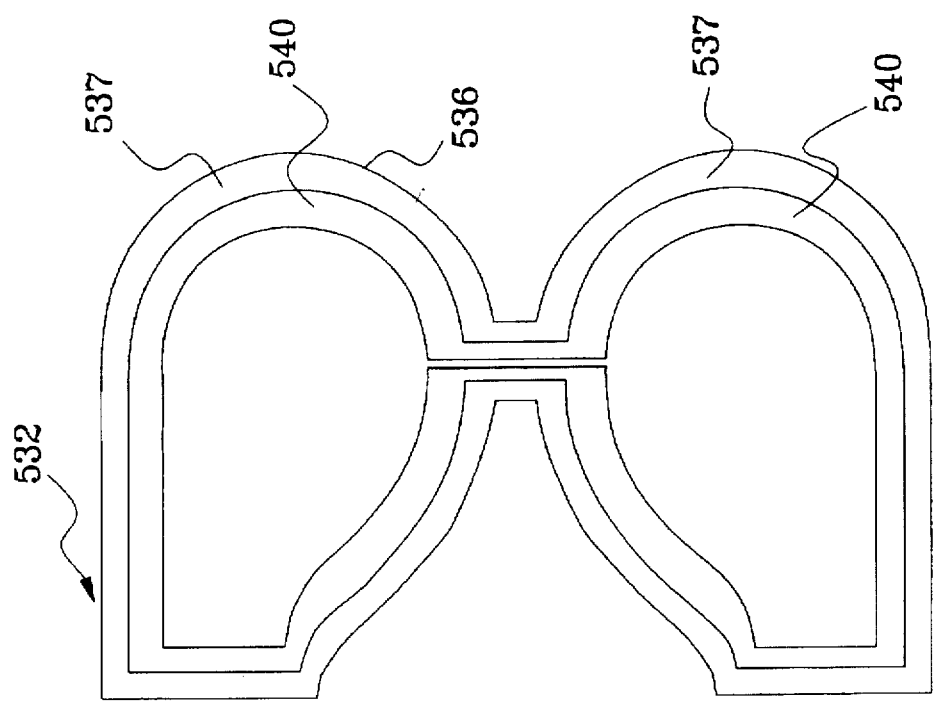
FIG. 17 is plan view of an alternative embodiment of the right lens shield of the inventive device.
Figure 16:
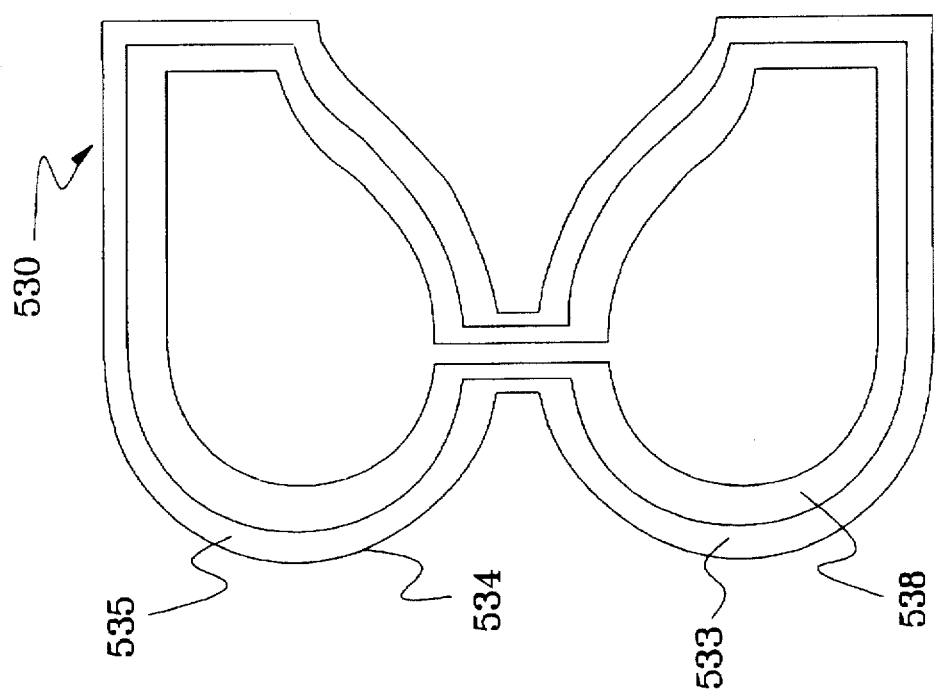
FIG. 16 is plan view of an alternative embodiment of the left lens shield of the inventive device.

FIGS. 16 and 17 show an alternative embodiment of the inventive shields 530 and 532 whereby adhesive 538 and 540 is applied to substrate 534 and 536 providing for an adhesive free periphery 535 and 537 to facilitate grasping by he user.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. Protective goggles, comprising:
   (a) a transparent protective member, said transparent member comprising:
      (i) a transparent lens, having opposite sides,
      (ii) a support structure, said support structure configured and dimensioned to support said lens in front of the eyes of a user;
   (b) a plurality of bendable transparent anti-fouling members which are bendable along a bend line and dimensioned to allow said anti-fouling members to be folded around and overlie said opposite sides of said lens; and
   c) an adhesive disposed on both sides of said bend line of said bendable transparent anti-fouling members, thereby allowing said transparent anti-fouling members to be adhered to both sides of said transparent protective member.

2. Protective gogles as in claim 1, wherein said adhesive is disposed such that an adhesive free area is provided on said transparent anti-fouling members.

3. Protective gogles as in claim 1, wherein said adhesive is disposed in at least two discrete areas on the periphery of said transparent anti-fouling members.

4. Protective gogles as in claim 1, wherein said adhesive is disposed only on a peripheral portion of said transparent anti-fouling members.

5. Protective gogles as in claim 1, wherein said transparent anti-fouling members are polarizing filters with a polarizing characteristic oriented to reduce glare.

6. Protective goggles as in claim 1, wherein said lens is sandwiched to a thin polarizing film.

7. Protective gogles as in claim 1, wherein said transparent anti-fouling members are comprised of plastic film.

8. Protective gogles as in claim 1, wherein said transparent anti-fouling members are comprised of polyethylene film.

9. Protective gogles as in claim 1, wherein said anti-fouling members are provided in a pad-like configuration.

10. Protective goggles as in claim 1, wherein said anti-fouling members are resistant to chemicals used in the workplace.

11. Protective goggles as in claim 1, wherein said adhesive is disposed on said transparent anti-fouling members.

12. Protective gogles as in claim 1, wherein said anti-fouling members are resistant to heat.

13. Protective goggles as in claim 1, wherein said protective goggles are resistant to heat.

14. Protective goggles as in claim 1, wherein said protective goggles are resistant to heat.

* * * * *